(12) United States Patent
Zhang et al.

(10) Patent No.: US 10,183,017 B2
(45) Date of Patent: *Jan. 22, 2019

(54) METHODS AND USES OF QUINOLINE DERIVATIVES IN THE TREATMENT OF SOFT TISSUE SARCOMAS AND PHARMACEUTICAL COMPOSITIONS FOR TREATMENT OF SAME

(71) Applicants: Chia Tai Tianqing Pharmaceutical Group Co., Ltd., Jiangsu (CN); Advenchen Laboratories Nanjing Ltd, Jiangsu (CN)

(72) Inventors: Xiquan Zhang, Jiangsu (CN); Xunqiang Wang, Jiangsu (CN); Xiaole Zhan, Jiangsu (CN); Jie Dai, Jiangsu (CN); Xin Tian, Jiangsu (CN); Ling Yang, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/953,184

(22) Filed: Apr. 13, 2018

(65) Prior Publication Data
US 2018/0235953 A1 Aug. 23, 2018

Related U.S. Application Data

(63) Continuation of application No. 15/315,647, filed as application No. PCT/CN2015/080870 on Jun. 5, 2015, now Pat. No. 9,968,597.

(30) Foreign Application Priority Data

Jun. 6, 2014 (CN) .......................... 2014 1 0249705

(51) Int. Cl.
*A61K 9/48* (2006.01)
*A61K 31/4709* (2006.01)

(52) U.S. Cl.
CPC ............ *A61K 31/4709* (2013.01); *A61K 9/48* (2013.01)

(58) Field of Classification Search
None
See application file for complete search history.

(56) References Cited

U.S. PATENT DOCUMENTS

| | | | |
|---|---|---|---|
| 7,667,039 B2 | 2/2010 | Garcia-Echeverria et al. |
| 8,148,532 B2 | 4/2012 | Chen |
| 9,550,781 B2 | 1/2017 | Xiao |
| 9,725,439 B2 | 8/2017 | Xiao et al. |
| 9,751,859 B2 | 9/2017 | Chen |
| 9,968,597 B2 | 5/2018 | Zhang et al. |
| 2010/0105696 A1 | 4/2010 | Garcia-Echevrria et al. |
| 2016/0326138 A1 | 11/2016 | Chen et al. |
| 2017/0174687 A1 | 6/2017 | Chen et al. |
| 2017/0182027 A1 | 6/2017 | Wang |
| 2017/0202828 A1 | 7/2017 | Zhang |
| 2017/0304290 A1 | 10/2017 | Wang et al. |
| 2018/0002311 A1 | 1/2018 | Chen et al. |

FOREIGN PATENT DOCUMENTS

| | | |
|---|---|---|
| CN | 101809012 | 8/2010 |
| CN | 102344438 | 2/2012 |
| WO | WO 2006/122806 | 11/2006 |
| WO | WO 2008/112407 | 9/2008 |
| WO | WO 2008/112408 | 9/2008 |
| WO | WO 2009/155527 | 12/2009 |
| WO | WO 2010/105761 | 9/2010 |
| WO | WO 2014/113616 | 7/2014 |

OTHER PUBLICATIONS

Bello, E. et al., E-3810 Is a Potent Dual Inhibitor of VEGFR and FGFR that Exerts Antitumor Activity in Multiple Preclinical Models, Cancer Research; 71(4), Feb. 15, 2011.
Moreno et al., "Tyrosine Kinase Inhibitors in Treating Soft Tissue Sarcomas: sunitinib in non-GIST sarcomas," Clin Transl Oncol (2010) 12:468-472.
Sala, F. et al., Development and validation of a high-performance liquid chromatography—tandem mass spectrometry method for the determination of the novel inhibitor of angiogenesis E-3810 in human plasma and its application in a clinical pharmacokinetic study, Journal of Mass Spectrometry, 2011, 46, pp. 1039-1045.
Traina et al.- Optimizing Chemotherapy Dose and Schedule by Norton-Simon Mathematical Modeling (in cited OA).
Zhou, Y. et al., AL3810, a multi-tyrosine kinase inhibitor, exhibits potent anti-angiogenic and ant-tumor activity via targeting VEGFR, FGFR, and PDGFR, Journal of Cellular and Molecular Medicine, vol. 16, No. 10, 2012 pp. 2321-2330.
U.S. Appl. No. 15/659,510, filed Jul. 25, 2017 including prosecution history.
U.S. Appl. No. 15/533,873, filed Jun. 7, 2017 including prosecution history.
Eskens et al, "Phase I Dose Escalation Study of Telatinib, a Tyrosine Kinase Inhibitor of Vascular Endothelial Growth Factor Receptor 2 and 3, Platelet-Derived Growth Factor Receptor β, and c-Kit, in Patients With Advanced or Metastatic Solid Tumors." Journal of Clinical Oncology (2009), vol. 27 (25), pp. 4169-4176.
Han et al., "Anlotinib as a third-line therapy in patients with refractory advanced non-small-cell lung cancer: a multicentre, randomized phase 11 trial (AL TER0302)", 2018, British Journal of Cancer, 118(5), pp. 654-661. (Year: 2018).

(Continued)

*Primary Examiner* — Karl J Puttlitz
(74) *Attorney, Agent, or Firm* — Knobbe, Martens, Olson & Bear, LLP

(57) ABSTRACT

The present invention addresses methods and uses of quinoline derivatives in the treatment of tumors and pharmaceutical compositions for treatment of same. Specifically, the present invention involves a method and applications for the use of the quinoline derivative 1-[[[4-(4-fluoro-2-methyl-H-indol-5-yl)oxy-6-methoxyquinolin-7-yl]oxy]methyl]cyclopropylamine in the treatment of soft tissue sarcomas and pharmaceutical compositions for treatment of same.

20 Claims, No Drawings

(56) References Cited

OTHER PUBLICATIONS

National Center for Biotechnology Information. PubChem Compound Database; CI D=25017 411, https://pubchem.ncbi .nlm.nih .gov/compound/25017 411 (accessed Apr. 4, 2018). (Year: 2018).
Sun et al., "Safety, pharmacokinetics, and antitumor properties of anlotinib, an oral multi-target tyrosine kinase inhibitor, in patients with advanced refractory solid tumors", 2016, Journal of Hematology & Oncology, 9: 105; DOI 10.1186/s 13045-016-0332-8. (Year: 2016).
XELODA® Prescribing Information; Genentech USA, Inc.,—Xeloda, Mar. 2015.

METHODS AND USES OF QUINOLINE DERIVATIVES IN THE TREATMENT OF SOFT TISSUE SARCOMAS AND PHARMACEUTICAL COMPOSITIONS FOR TREATMENT OF SAME

INCORPORATION BY REFERENCE TO ANY PRIORITY APPLICATIONS

This application is a continuation of U.S. application Ser. No. 15/315,647, filed Dec. 1, 2016, issued as U.S. Pat. No. 9,968,597, which is the U.S. National Phase of International Application PCT/CN2015/080870, filed Jun. 5, 2015, which claims the benefit of priority to Chinese Application No. 201410249705.7, filed on Jun. 6, 2014. All of the foregoing applications are fully incorporated herein by reference in their entireties for all purposes.

FIELD OF THE INVENTION

The present invention belongs to the field of medicine, and the present invention relates to a method and use of quinoline derivatives in treatment of tumours and a pharmaceutical composition for treatment of the same. More specifically, the present invention relates to a method and use of quinoline derivatives in treatment of soft tissue sarcomas and a pharmaceutical composition for treatment of soft tissue sarcomas.

BACKGROUND OF THE INVENTION

Soft tissue sarcomas (STS) are a group of rare malignant tumours arising from mesenchymal cells, which can occur at any age, and have no significant gender difference, and have a wide distribution and different histological appearance. Although the proportion of STS is less than 1% in adult malignant tumours and 15% in childhood malignant tumours, about 50% STS patients would have distant metastasis, even death.

The pathogeny of soft tissue sarcomas is still unclear, it is generally believed that soft tissue sarcomas is caused by many factors, and currently, it is known that a small number of genetic factors have a correlation with pathogenesis of certain soft tissue sarcomas. The progress of STS is a course gradually spreading from local portion(s) to the whole body, characterized by tumidness and/or deep masses. The local period of soft tissue sarcomas occurred in adult patients or some children patients has a longer duration. The most frequently metastatic site is lung, followed by bones, liver, etc., whereas regional lymph nodes are less involved.

Common soft tissue sarcomas include malignant fibrous histiocytoma, fibrosarcoma, liposarcoma, leiomyosaroma of soft tissue, rhabdomyosarcoma, and synovial sarcoma. Other soft tissue sarcomas also include dermatofibrosarcoma protuberans, malignant peripheral nerve sheath tumor, alveolar soft-part sarcoma, clear cell sarcoma, hemangiosarcoma, malignant mesenchymoma, epithelioid sarcoma, undifferentiated sarcoma and the like.

Malignant fibrous histiocytoma (MFH) is the sarcoma arising from tissue cells, generally consisting of both of tissue cells and fibroblast.

Fibrosarcoma is a malignant tumor consisting of fibrocyte and fiber produced thereby, and has a relatively single morphology and herringbone structure.

Liposarcoma is a soft tissue malignant tumour, characterized by differentiation of tumour cells to lipoblasts and manifesting as the existence of atypical lipoblasts in different differentiation stages.

Leiomyosaroma of soft tissue is a malignant tumour occurred in smooth muscle cells or mesenchymal cells having differentiation potential to smooth muscle cells.

Rhabdomyosarcoma (RMS) is a soft tissue malignant tumour arising from primary mesenchymal cells differentiating into striated muscle, and consisting of different differentiation grades of striated muscle metrocyte. The incidence of rhabdomyosarcoma is higher in male than in female. The onset age range is quite considerable, and it could onset from the newborns to the elderly, most frequently in children. Rhabdomyosarcoma is the one having higher malignancy in soft tissue sarcomas with a poor prognosis.

Synovial sarcoma (SS) is a malignant tumour in which the tumour cells show two-way differentiation, wherein epithelioid cells form cleft and atypical glandular cavity, and spindle cells generate reticular fibers and collagen fibers. The incidence of synovial sarcoma in soft tissue sarcomas is in the middle level.

Alveolar soft-part sarcoma (ASPS) is a soft tissue malignant tumour with uncertain histogenesis, and it has unique histological appearance of pseudo secretory-like structure showing alveolar and is a rare tumour.

Currently, the treatment of soft tissue sarcomas emphasizes multidisciplinary synthetic therapy primarily based on surgery. Surgery or the combination with radiotherapy is the main treatment method of soft tissue sarcomas with low-grade malignancy, while as for the patients with advanced soft tissue sarcomas having distant metastasis, chemotherapy is the main method for treatment. Since STS frequently spread into the whole body and pulmonary metastasis may occur in its early stage, surgery is still recommended for isolated pulmonary metastasis focuses, other metastasis focuses need drug therapy. It is especially important to select appropriate drug therapy for patients with advanced refractory STS being unsuitable for surgery or having tolerance to commonly used chemotherapy drugs.

At present, there are a few chemotherapeutics effective against STS, including anthracyclines, such as adriamycin, doxorubicin, epirubicin, pirarubicin and the like; and alkylating drugs, such as cyclophosphamide, ifosfamide, decarbazine and the like. The effective rate of single drug is 14%-30%. Adriamycin and ifosfamide show the best therapeutic effect for first-line chemotherapy. Although all the above drugs can effectively treat STS, the following factors such as safety and tolerance of the drugs limit the application of such drugs in treating advanced, relapsed and refractory STS, and there is an urgent clinical need to develop new second-line drugs for treatment of STS.

In April 2012, the FDA approves Pazopanib (Votrient) of GSK for use of treating patients with advanced soft tissue sarcomas who have been treated with chemotherapy.

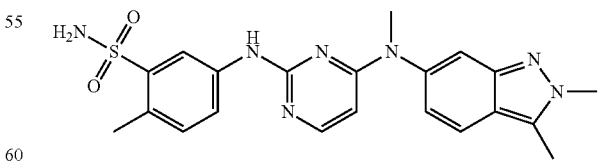

Pazopanib

Since soft tissue sarcomas is a rare heterogeneous group of tumours, treatment is usually more complex, the drugs and the programs for treatment available are limited yet, thus developing more new therapeutic drugs having strong specificity, target specificity, little side-effect and significant efficiency is required, so as to achieve desirable therapeutic effects.

SUMMARY OF THE INVENTION

In the first aspect, the present invention provides a method for treating soft tissue sarcomas, which comprises administrating a therapeutically effective amount of Compound I or pharmaceutically acceptable salts thereof to patients in need of treatment.

In another aspect, the present invention provides a use of Compound I or pharmaceutically acceptable salts thereof in manufacturing a medicament for treating soft tissue sarcomas.

In yet another aspect, the present invention provides a pharmaceutical composition for treatment of soft tissue sarcomas, which comprises Compound I or pharmaceutically acceptable salts thereof, and at least one pharmaceutically acceptable carrier.

Said soft tissue sarcomas include, but not limited to, malignant fibrous histiocytoma, fibrosarcoma, liposarcoma, leiomyosaroma of soft tissue, rhabdomyosarcoma, synovial sarcoma, dermatofibrosarcoma protuberans, malignant peripheral nerve sheath tumor, alveolar soft-part sarcoma, clear cell sarcoma, hemangiosarcoma, malignant mesenchymoma, epithelioid sarcoma and undifferentiated sarcoma.

DETAILED EMBODIMENTS OF THE INVENTION

In the first aspect, the present invention provides a method for treating soft tissue sarcomas, which comprises administrating a therapeutically effective amount of Compound I or pharmaceutically acceptable salts thereof to patients in need of treatment. Said soft tissue sarcomas include, but not limited to, malignant fibrous histiocytoma, fibrosarcoma, liposarcorna, leiomyosaroma of soft tissue, rhabdomyosarcoma, synovial sarcoma, dermatofibrosarcoma protuberans, malignant peripheral nerve sheath tumor, alveolar soft-part sarcoma, clear cell sarcoma, hemangiosarcoma, malignant mesenchymoma, epithelioid sarcoma and undifferentiated sarcoma.

In one embodiment of the present invention, a method for treating advanced soft tissue sarcomas is provided. In one embodiment of the present invention, a method for treating advanced soft tissue sarcomas which have been treated with chemotherapy is provided.

The chemical name of Compound I is 1-[[[4-(4-fluoro-2-methyl-1H-indol-5-yl)oxy-6-methoxyquinolin-7-yl]oxy]methyl]cyclopropylamine, which has the following structural formula:

Compound I

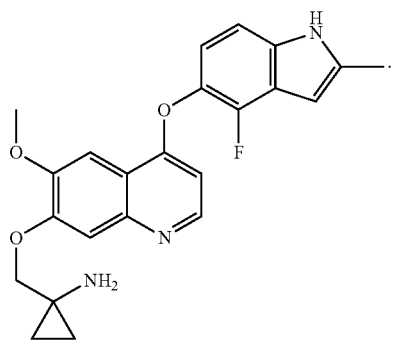

Compound I can be administrated in the free base form thereof, and also can be administrated in the form of salts, hydrates and prodrugs thereof (the prodrugs will be converted into the free base form of Compound I in vivo). For example, the pharmaceutically acceptable salts of Compound I are within the scope of the present invention, and the salts can be produced from different organic acids and inorganic acids according to well-known processes in the art.

In some embodiments, Compound I is administrated in the form of hydrochloride thereof. In some embodiments, Compound I is administrated in the form of monohydrochloride thereof. In some embodiments, Compound I is administrated in the form of dihydrochloride thereof. In some embodiments, Compound I is administrated in the crystal form of hydrochloride thereof. In a certain embodiment, Compound I is administrated in the crystal form of dihydrochloride thereof.

Compound I or pharmaceutically acceptable salts thereof can be administrated via various administration routes, and the routes include, but not limited to, the one selected from the following routes: orally, parenterally, intraperitoneally, intravenously, intraarterially, transdermally, sublingually, intramuscularly, rectally, transbuccally, intranasally, via inhalation, vaginally, intraoccularly, via local administration, subcutaneously, intraadiposally, intraarticularly, intraperitoneally or intrathecally. In a certain embodiment, the administration is performed orally.

The administration amount of Compound I or pharmaceutically acceptable salts thereof can be determined according to severity of diseases, response of diseases, any treatment-related toxicity, and age and health status of patients. In some embodiments, the daily administration dosage of Compound I or pharmaceutically acceptable salts thereof is 2 mg-20 mg. In some embodiments, the daily administration dosage of Compound I or pharmaceutically acceptable salts thereof is 5 mg-20 mg. In some embodiments, the daily administration dosage of Compound I or pharmaceutically acceptable salts thereof is 8 mg-20 mg. In some embodiments, the daily administration dosage of Compound I or pharmaceutically acceptable salts thereof is 10 mg-16 mg. In some embodiments, the daily administration dosage of Compound I or pharmaceutically acceptable salts thereof is 10 mg-14 mg. In a certain embodiment, the daily administration dosage of Compound I or pharmaceutically acceptable salts thereof is 10 mg. In a certain embodiment, the daily administration dosage of Compound I or pharmaceutically acceptable salts thereof is 12 mg. In a certain embodiment, the daily administration dosage of Compound I or pharmaceutically acceptable salts thereof is 14 mg. In a certain embodiment, the daily administration dosage of Compound I or pharmaceutically acceptable salts thereof is 16 mg.

Compound I or pharmaceutically acceptable salts thereof can be administrated one or more time daily. In some embodiments, Compound I or pharmaceutically acceptable salts thereof is administrated once per day. Compound I or pharmaceutically acceptable salts thereof can also be administrated in the form of single dosage. In one embodiment, the administration is performed once per day. In one embodiment, the administration is performed once per day in the form of single dosage. In one embodiment, the administration is performed once per day in single dosage of oral solid formulations.

Administration methods can be generally determined according to activities and toxicities of drugs, and tolerability of patients and the like. Preferably, Compound I or pharmaceutically acceptable salts thereof is administrated in the manner of interval administration.

The interval administration includes administration periods and rest periods, and during the administration periods, Compound I or pharmaceutically acceptable salts thereof can be administrated one or more times daily. For example, Compound I or pharmaceutically acceptable salts thereof is administrated daily in an administration period, and then the administration is stopped for a period of time in a rest period, followed by an administration period and then a rest period, such an administration regimen can be repeated many times. Among them, the ratio of the administration periods to the rest periods in days is 2:0.5-5, preferably 2:0.5-3, more preferably 2:0.5-2, and most preferably 2:0.5-1.

In some embodiments, the administration is continuously performed for 2 weeks and rest for 2 weeks. In some embodiments, the administration is continuously performed once daily for 14 days and rest for 14 days, followed by continuous administrating once daily for 14 days and resting for 14 days, such an administration regimen with two-week continuous administration periods and two-week rest periods can be repeated many times.

In some embodiments, the administration is continuously performed for 2 weeks and rest for 1 week. In some embodiments, the administration is continuously performed once daily for 14 days and rest for 7 days, followed by continuous administrating once daily for 14 days and resting for 7 days, such an administration regimen with two-week continuous administration periods and one-week rest periods can be repeated many times.

In some embodiments, the administration is continuously performed for 5 days and rest for 2 days. In some embodiments, the administration is continuously performed once daily for 5 days and rest for 2 days, followed by continuous administrating once daily for 5 days and resting for 2 days, such an administration regimen with five-day continuous administration periods and two-day rest periods can be repeated many times.

In one embodiment, Compound I or pharmaceutically acceptable salts thereof is separately administrated to patients as the sole active ingredient.

In another aspect, the present invention provides a use of Compound I or pharmaceutically acceptable salts thereof in manufacturing a medicament for treating soft tissue sarcomas. Among them, said soft tissue sarcomas include, but not limited to malignant fibrous histiocytoma, fibrosarcoma, liposarcoma, leiomyosaroma of soft tissue, rhabdomyosarcoma, synovial sarcoma, dermatofibrosarcoma protuberans, malignant peripheral nerve sheath tumor, alveolar soft-part sarcoma, clear cell sarcoma, hemangiosarcoma, malignant mesenchymoma, epithelioid sarcoma and undifferentiated sarcoma.

In one embodiment, a use of Compound I or pharmaceutically acceptable salts thereof in manufacturing a medicament for treating advanced soft tissue sarcomas is provided.

In one embodiment, a use of Compound I or pharmaceutically acceptable salts thereof in manufacturing a medicament for treating advanced soft tissue sarcomas which have been treated with chemotherapy is provided.

Compound I can be the free base form thereof, and can also be in the form of salts, hydrates and prodrugs thereof (the prodrugs will be converted into the free base form of Compound I in vivo). For example, the pharmaceutically acceptable salts of Compound I are within the scope of the present invention, and the salts can be produced from different organic acids and inorganic acids according to well-known processes in the art.

In some embodiments, Compound I or pharmaceutically acceptable salts thereof is the form of hydrochloride of Compound I. In some embodiments, Compound I or pharmaceutically acceptable salts thereof is the form of monohydrochloride of Compound I. In some embodiments, Compound I or pharmaceutically acceptable salts thereof is the form of dihydrochloride of Compound I. In some embodiments, Compound I or pharmaceutically acceptable salts thereof is the crystal form of hydrochloride of Compound I. In a certain embodiment, Compound I or pharmaceutically acceptable salts thereof is the crystal form of dihydrochloride of Compound I.

The amount of Compound I or pharmaceutically acceptable salts thereof can be determined according to severity of diseases, response of diseases, any treatment-related toxicity, and age and health status of patients. In some embodiments, the amount of Compound I or pharmaceutically acceptable salts thereof is 2 mg-20 mg. In some embodiments, the amount of Compound I or pharmaceutically acceptable salts thereof is 5 mg-20 mg. In some embodiments, the amount of Compound I or pharmaceutically acceptable salts thereof is 8 mg-20 mg. In some embodiments, the amount of Compound I or pharmaceutically acceptable salts thereof is 10 mg-16 mg. In some embodiments, the amount of Compound I or pharmaceutically acceptable salts thereof is 10 mg-14 mg. In a certain embodiment, the amount of Compound I or pharmaceutically acceptable salts thereof is 10 mg. In a certain embodiment, the amount of Compound I or pharmaceutically acceptable salts thereof is 12 mg. In a certain embodiment, the amount of Compound I or pharmaceutically acceptable salts thereof is 14 mg. In a certain embodiment, the amount of Compound I or pharmaceutically acceptable salts thereof is 16 mg.

In yet another aspect, the present invention provides a pharmaceutical composition for treatment of soft tissue sarcomas, and the pharmaceutical composition comprises Compound I or pharmaceutically acceptable salts thereof, and at least one pharmaceutically acceptable carrier.

Said soft tissue sarcomas include, but not limited to malignant fibrous histiocytoma, fibrosarcoma, liposarcoma, leiomyosaroma of soft tissue, rhabdomyosarcoma, synovial sarcoma, dermatofibrosarcoma protuberans, malignant peripheral nerve sheath tumor, alveolar soft-part sarcoma, clear cell sarcoma, hemangiosarcoma, malignant mesenchymoma, epithelioid sarcoma and undifferentiated sarcoma.

In some embodiments of the present invention, a pharmaceutical composition for treatment of advanced soft tissue sarcomas is provided.

In some embodiments of the present invention, a pharmaceutical composition for treatment of advanced soft tissue sarcomas which have been treated with chemotherapy is provided.

Compound I can be the free base form thereof, and can also be in the form of salts, hydrates and prodrugs thereof (the prodrugs will be converted into the free base form of Compound I in vivo). For example, the pharmaceutically acceptable salts of Compound I are within the scope of the present invention, and the salts can be produced from different organic acids and inorganic acids according to well-known processes in the art.

In some embodiments, Compound I or pharmaceutically acceptable salts thereof is the form of hydrochloride of Compound I. In some embodiments, Compound I or pharmaceutically acceptable salts thereof is the form of monohydrochloride of Compound I. In some embodiments, Compound I or pharmaceutically acceptable salts thereof is the form of dihydrochloride of Compound I. In some embodiments, Compound I or pharmaceutically acceptable salts thereof is the crystal form of hydrochloride of Compound I. In a certain embodiment, Compound I or pharmaceutically acceptable salts thereof is the crystal form of dihydrochloride of Compound I.

The amount of Compound I or pharmaceutically acceptable salts thereof can be determined according to severity of diseases, response of diseases, any treatment-related toxicity, and age and health status of patients. In some embodiments, the amount of Compound I or pharmaceutically acceptable salts thereof in the pharmaceutical composition is 2 mg-20 mg. In some embodiments, the amount of Compound I or pharmaceutically acceptable salts thereof is 5 mg-20 mg. In some embodiments, the amount of Compound I or pharmaceutically acceptable salts thereof in the pharmaceutical composition is 8 mg-20 mg. In some embodiments, the amount of Compound I or pharmaceutically acceptable salts thereof is 10 mg-16 mg. In some embodiments, the amount of Compound I or pharmaceutically acceptable salts thereof is 10 mg-14 mg. In a certain embodiment, the amount of Compound I or pharmaceutically acceptable salts thereof is 10 mg. In a certain embodiment, the amount of Compound I or pharmaceutically acceptable salts thereof is 12 mg. In a certain embodiment, the amount of Compound I or pharmaceutically acceptable salts thereof is 14 mg. In a certain embodiment, the amount of Compound I or pharmaceutically acceptable salts thereof is 16 mg.

In some embodiments of the present invention, the pharmaceutical compositions are the formulations suitable for oral administration, which include tablets, capsules, dusts, granulates, drip pills, pastes, powders and the like, and tablets and capsules are preferred. Among them, the tablets can be common tablets, dispersible tablets, effervescent tablets, sustained release tablets, controlled release tablets or enteric coated tablets, and the capsules can be common capsules, sustained release capsules, controlled release capsules or enteric coated capsules. The oral formulation can be prepared with well-known pharmaceutically acceptable carriers in the art by conventional methods. The pharmaceutically acceptable carriers include bulking agents, absorbing agents, wetting agents, binding agents, disintegrating agents, lubricants and the like. The bulking agents include starch, lactose, mannitol, microcrystalline cellulose or the like; the absorbing agents include calcium sulfate, calcium hydrogen phosphate, calcium carbonate or the like; the wetting agents include water, ethanol or the like; the binding agents include hydroxypropyl methylcellulose, povidone, microcrystalline cellulose or the like; the disintegrating agents include cross-linked carboxymethyl cellulose sodium, crospovidone, surfactants, low-substituted hydroxypropyl cellulose or the like; the lubricants include magnesium stearate, talc powder, polyethylene glycol, sodium dodecylsulfate, Aerosil, talc powder or the like. The pharmaceutical excipients also include colorants, sweetening agents and the like.

In one embodiment, the pharmaceutical composition is solid formulations suitable for oral administration. For example, the composition can be in the form of tablets and capsules. In a certain embodiment, the pharmaceutical composition is capsules. In a certain composition of the present invention, the pharmaceutically acceptable carriers of the oral solid formulations include mannitol, microcrystalline cellulose, hydroxypropyl cellulose, and magnesium stearate.

In one embodiment, a pharmaceutical composition for treating soft tissue sarcomas being formulated into a form of single dosage is provided. In one embodiment, the form of single dosage contains 2 mg-20 mg of Compound I or pharmaceutically acceptable salts thereof. In some embodiments, the form of single dosage contains 5 mg-20 mg of Compound I or pharmaceutically acceptable salts thereof. In one embodiment, the form of single dosage contains 8 mg-20 mg of Compound I or pharmaceutically acceptable salts, preferably 10 mg-16 mg of Compound I or pharmaceutically acceptable salts, and more preferably 10 mg-14 mg of Compound I or pharmaceutically acceptable salts. In a certain embodiment, the pharmaceutical composition contains 10 mg of Compound I or pharmaceutically acceptable salts thereof. In a certain embodiment, the pharmaceutical composition contains 12 mg of Compound I or pharmaceutically acceptable salts thereof. In a certain embodiment, the pharmaceutical composition contains 14 mg of Compound I or pharmaceutically acceptable salts thereof. In a certain embodiment, the pharmaceutical composition contains 16 mg of Compound I or pharmaceutically acceptable salts thereof.

Preferably, the pharmaceutical composition is administrated in an interval administration regimen. The interval administration includes administration periods and rest periods, and during the administration periods, the pharmaceutical composition can be administrated one or more times daily. For example, the pharmaceutical composition is administrated daily in an administration period, and then the administration is stopped for a period of time in a rest period, followed by an administration period and then a rest period, such an administration regimen can be repeated many times. Among them, the ratio of the administration periods to the rest periods in days is 2:0.5-5, preferably 2:0.5-3, more preferably 2:0.5-2, and most preferably 2:0.5-1.

In some embodiments, the administration is continuously performed for 2 weeks and rest for 2 weeks. In some embodiments, the administration is continuously performed once daily for 14 days and rest for 14 days, followed by continuous administrating once daily for 14 days and resting for 14 days, such an administration regimen with two-week continuous administration periods and two-week rest periods can be repeated many times.

In some embodiments, the administration is continuously performed for 2 weeks and rest for 1 week. In some embodiments, the administration is continuously performed once daily for 14 days and rest for 7 days, followed by continuous administrating once daily for 14 days and resting for 7 days, such an administration regimen with two-week continuous administration periods and one-week rest periods can be repeated many times.

In some embodiments, the administration is continuously performed for 5 days and rest for 2 days. In some embodiments, the administration is continuously performed once daily for 5 days and rest for 2 days, followed by continuous administrating once daily for 5 days and resting for 2 days, such an administration regimen with five-day continuous administration periods and two-day rest periods can be repeated many times.

Herein, unless indicated otherwise, the dosages and ranges provided therein are based on the molecular weight of the free base form of Compound I.

Herein, the crystal form of the hydrochloride of Compound I includes, but not limited to, Forms A, B and C crystal disclosed in the Chinese patent application publication No. CN102344438A, wherein Forms A and B crystal are those which do not contain crystal water and other solvents basically, and Form C crystal is the one containing two molecules of crystal water. In some embodiments, the crystal form of the dihydrochloride of Compound I is Form A crystal.

Unless indicated otherwise, for the purpose of the present application, the following terms are intended to have the meanings denoted below as used in the Description and Claims.

"Patients" refer to mammal, preferably human. In some embodiments, the patients are those having failed standard treatment or lacking standard treatment.

"Pharmaceutically acceptable" means that which is useful in preparing a pharmaceutical composition that is generally safe, non-toxic and neither biologically nor otherwise undesirable, and includes that which is acceptable for human pharmaceutical use.

"Pharmaceutically acceptable salts" include, but not limited to acid addition salts formed from inorganic acids such as hydrochloric acid, hydrobromic acid, sulfuric acid, nitric acid, phosphoric acid or the like; or acid addition salts formed from organic acids such as acetic acid, trifluoroacetic acid, propionic acid, caproic acid, heptanoic acid, cyclopentane propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methyl sulfonic acid, ethyl sulfonic acid, 1,2-ethanedisulfonic acid, 2-hydroxyethanesulphonic acid, benzenesulfonic acid, p-chlorobenzenesulfonic acid, p-toluenesulfonic acid, 3-phenylpropionic acid, trimethylacetic acid, t-butylacetic acid, dodecyl sulfuric acid, gluconic acid, glutamic acid, hydroxynaphthoic acid, salicylic acid, stearic acid and the like.

"Therapeutically effective amount" means an amount of a compound that, when administered to a subject for treating a disease state, is sufficient to effect such treatment for the disease state.

"Treatment/treating" means any administration of therapeutically effective amount of a compound, and includes:

(1) Inhibiting the disease in humans that is experiencing or displaying the pathology or symptomatology of the disease (i.e., retarding further development of the pathology and/or symptomatology), or (2) Ameliorating the disease in humans that is experiencing or displaying the pathology or symptomatology of the disease (i.e., reversing the pathology and/or symptomatology).

"DCR" refers to disease control rate (i.e., no progression of disease).

"PR" refers to partial remission, and specifically means 30% or more decrease in the sum of the diameters of target lesions of tumours than the baseline level.

"PD" refers to progression of disease, and specifically means 20% or more increase in the sum of the diameters of target lesions of tumours than the baseline level.

"SD" refers to stable disease, and specifically means that the decrease degree of target lesions of tumours does not reach the PR level, and the increase degree does not reach the PD level either, falling somewhere therebetween.

"ORR" refers to overall response rates, and specifically means the percentage ratio of the cases which reach PR to the total qualified cases in tumour assessment.

"PFS" refers to progression free survival.

EXAMPLES

Example 1 1-[[[4-(4-fluoro-2-methyl-1H-indol-5-yl)oxy-6-methoxyquinolin-7-yl]oxy]methyl]cyclopropylamine dihydrochloride

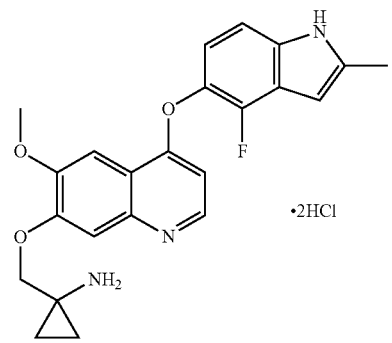 [SMILES: COc1cc2c(Oc3ccc4[nH]c(C)cc4c3F)ccnc2cc1OCC1(N)CC1]

1-[[[4-(4-fluoro-2-methyl-1H-indol-5-yl)oxy-6-methoxyquinolin-7-yl]oxy]methyl]cyclopropylamine was prepared by reference to the method of Example 24 in WO2008112407, and then the title compound was prepared by reference to the preparation method in "Examples of Salt Formation" of the Description of WO2008112407.

Alternatively, the title compound was prepared by reference to the method disclosed in the Chinese patent application publication No. CN102344438A.

Example 2 The Capsules Comprising 1-[[[4-(4-fluoro-2-methyl-1H-indol-5-yl)oxy-6-methoxyquinolin-7-yl]oxy]methyl]cyclopropylamine dihydrochloride (dihydrochloride of Compound I)

| Raw material/excipient names | amount (1000 capsules) |
|---|---|
| Dihydrochloride of Compound I | 14.16 g (corresponding to 12 g Compound I) |
| Mannitol | 89 g |
| Microcrystalline cellulose | 138.4 g |
| Hydroxypropyl cellulose | 5.9 g |
| Magnesium stearate | 0.99 g |

Dihydrochloride of Compound I was grinded and sifted with a 80 mesh sieve, and then mixed uniformly with mannitol and hydroxypropyl cellulose; the prescribed amount of microcrystalline cellulose was subsequently added, mixed uniformly and sifted with a 0.8 mm sieve; and finally, the prescribed amount of magnesium stearate was added and mixed uniformly, and the obtained mixture was filled into capsules.

The capsules in which dihydrochloride of Compound I is at different contents can be prepared by reference to the above proportion and formulation.

Example 3 Tolerance of the Capsules of Dihydrochloride of Compound I and Preliminary Therapeutic Effect Study of Administration (1) Results of Tolerance Research The malignant tumor patients those were diagnosed definitely and had failed standard treatment or lacking standard treatment were recruited, continuous administrating for 2 weeks and resting for 1 week were applied, i.e., 3 weeks (21 days) was a treatment cycle, and the observation of tolerance was continuously performed and maintained at least 2 cycles (42 days), and the observation of therapeutic effects was performed at the same time.

When the administration was performed at 10 mg once daily, the adverse reactions occurred in 3 patients including grade III or above increased fatty and amylase in 1 case, and grade II asthenia in 1 case, and other grade I adverse reactions including hoarseness in 2 cases, diarrhea and abdominal pain in 1 case, hypertension in 1 case and the like.

Under the condition that the administration was performed at 16 mg once daily, 1 case in 3 patients occurred grade III elevation of blood pressure and asthenia when administrated at the $2^{nd}$ week in the $2^{nd}$ cycle.

Other adverse reactions occurred in this research group included grade II hypertension in 1 case, decreased thyroid function in 2 cases, increased ALT in 1 case, grade I increased triglyceride in 2 cases, diarrhea and abdominal pain in 2 cases, hand-foot syndrome in 1 case, hoarseness in 1 case and the like.

When the administration was performed at 12 mg once daily, a total of 18 patients (5 cases of them were out of the group) were observed in this group. The different degrees of adverse reactions occurred during administration. The order of severity was grade I or II, and no grade III or higher adverse reactions occurred. The specific situation included:
Blood fat: increased triglyceride in 8 cases, and increased total cholesterol in 7 cases;
Liver function: increased total bilirubin in 4 cases, increased ALT in 4 cases, increased AST in 5 cases, and increased creatinine in 1 case;
Dermal toxicity: hand-foot skin reaction in 6 cases, and rash in 4 cases;
Endocrine system: hypothyroidism in 7 cases, hyperthyroidism in 2 cases, increased amylase in 3 cases, and increased CK-MB in 2 cases;
Symptoms: asthenia in 6 cases, hoarseness in 4 cases, diarrhea in 6 cases, dizziness and headache in 2 cases, toothache in 3 cases, muscular soreness in 3 cases, nausea and loss of appetite in 3 cases, and tinnitus, fever and insomnia each in 1 case;
Others: hypertension in 5 cases, hematuria in 5 cases, proteinuria in 5 cases, and decreased WBC in 3 cases.
(2) Preliminary Therapeutic Effects on Soft Tissue Sarcomas Soft tissue sarcomas (the administration was continuously performed at 12 mg once daily for 2 weeks and rested for 1 week): a total of 8 subjects, the tumour evaluation of 1 case was PR (partial remission) after 4 cycles, 4 cases were SD (stable), 3 subjects were PD (progression of disease); and the clinical benefit rate of soft tissue sarcoma reached 62%.

The dosages involved in this Example were calculated based on the free base of Compound I.

The capsules of hydrochloride of Compound I were administrated by employing the administration regimen of continuous administration at 12 mg per day for two weeks and rested for one week, the general tolerability was very well, the adverse reaction was ½ degree and no other unintended adverse reaction was observed; for the therapeutic effects, soft tissue sarcomas benefited from the treatment.

Example 4 Therapeutic Effect Studies of the Capsules of Dihydrochloride of Compound I for Treating Soft Tissue Sarcomas From May 2013, phase II clinical studies about treating advanced soft tissue sarcomas in which the conventional therapy showed ineffective, with the capsules of dihydrochloride of Compound I were carried out in 15 centers in China. The studies applied Simon two-phase design, and the progression-free rate of the diseases for 12 weeks was the main indicator of the therapeutic effects; the conditions of the subjects who can be recruited into the group were: 1) the age of 18-70; and 2) at least one chemotherapy regimen (including antharcyclines) had been used to treat, and evaluated as progression of disease according to the therapeutic effect evaluation criteria of solid tumour (RECIST 1.1) over 6 months.

The qualified subjects took one capsule of dihydrochloride of Compound I (12 mg) once daily. The oral administration was continuously performed for 2 weeks and rested for 1 week, i.e., 3 weeks (21 days) was a treatment cycle. When the researchers considered that the patients was unsuitable for continuous administration, or evaluated as PD (progression of disease), or intolerance to adverse events based on the standard of RECIST 1.1, the administration stopped and the patients were out of the group. Table 1 shows the situations of therapeutic effects of each tumour subtype up to February 2015.

TABLE 1

Situations of therapeutic effects of each tumour subtype

| Tumour subtype and therapeutic effects | Total | Malignant fibrous histiocytoma | Liposarcorna | Leiomyosaroma | Synovial Sarcoma | Alveolar soft-part Sarcoma | Epithelioid Sarcoma | Fibrosarcoma | Clear cell Sarcoma | Undifferentiated Sarcoma | Others |
|---|---|---|---|---|---|---|---|---|---|---|---|
| Qualified subjects (case) | 165 | 18 | 11 | 24 | 48 | 14 | 6 | 20 | 7 | 4 | 13 |
| DCR of 12 weeks (case) | 98 | 9 | 7 | 17 | 32 | 12 | 3 | 12 | 3 | 1 | 2 |
| DCR of 12 weeks (%) | 59.39 | 50.00 | 63.64 | 70.83 | 66.67 | 85.71 | 50.00 | 60.00 | 42.86 | 25.00 | 15.38 |
| DCR of 24 weeks (case) | 55 | 2 | 3 | 10 | 17 | 11 | 2 | 6 | 3 | — | 1 |
| DCR of 24 weeks (%) | 33.33 | 11.11 | 27.27 | 41.67 | 35.42 | 78.57 | 33.33 | 30.00 | 42.86 | — | 7.69 |
| PR (case) | 20 | 1 | 1 | 1 | 8 | 7 | — | 1 | 1 | — | — |
| ORR (%) | 12.12 | 5.56 | 9.09 | 4.17 | 16.67 | 50.00 | — | 5.00 | 14.29 | — | — |
| Median PFS (day) | 84 | 83 | 122 | 105 | 97 | 165.5 | — | 84 | — | — | — |

In the above table, "—" represents that this data has not been calculated.
The dosages involved in this Example were calculated based on the free base of Compound I.

Example 5 Therapeutic Effects of the Capsules of Dihydrochloride of Compound I on Synovial Sarcoma (1) Patient's Medical History Female, born in 1986, synovial sarcoma on the left hip, post-operate local recurrence and double-pulmonary metastases, the pathological stage was pG2T2bN0M1, and the clinical stage was stage IV.

In April 2013, under no obvious predisposing causes, the pain over the left hip occurred without fever, CT examination was carried out and the results showed that: space occupying disease of the left posterior hip joint, with undetermined properties; the resection of the mass in the left hip was performed in April 2013, it was found in the surgery that the tumours were connected with the periost on the greater trochanter of femur, and the pathology after the surgery indicated synovial sarcoma of spindle cells in the left posterior hip joint. The chemotherapy regimen of ADM (adriamycin)+IFO (ifosfamide) was performed in May 2013, and during the chemotherapy, the patient had severe gastrointestinal reaction and grade IV bone marrow suppression; thus the chemotherapy regimen was changed as the single-drug chemotherapy with GEM (gemcitabine) in June 2013, the last time of chemotherapy was Sep. 30, 2013, the responses to chemotherapy were tolerable, a re-examination with chest CT during chemotherapy showed stable double-pulmonary metastasis; subsequently, the patient carried out a re-examination with pelvic magnetic resonance imaging, indicating that there was the possibility of tumor recurrence; and in January 2014, chest CT showed a progression of intrapulmonary lesions.

From Jan. 22, 2014, the capsules of dihydrochloride of Compound I were taken at 12 mg once daily, and the administration was continuously performed for 2 weeks and rested for 1 week, i.e., 3 weeks (21 days) was a treatment cycle.

(2) Tumour Baseline Evaluation Results

| Time | Sum of the longest diameter of target lesions (mm) | Medial basal segment of lower lobe in the right lung (mm) | Left gluteus maximus (mm) |
|---|---|---|---|
| Before treatment | 60 | 15 | 45 |
| Treatment with the capsules of dihydrochloride of Compound I for 2 cycles | 48 | 8 | 40 |
| Treatment with the capsules of dihydrochloride of Compound I for 6 cycles | 42 | 7 | 35 |

After the patient was administrated for 2 cycles, the sum of the longest diameter of target lesions decreased 20%; after the administration was performed for 6 cycles, the sum of the longest diameter of target lesions decreased 30% and PR (partial remission) was obtained, and thus the therapeutic effects were significant; during treating, non-target lesions had no progression. During administration, the adverse reactions were basically tolerable, and the main adverse event was gastrointestinal reaction, and no drug-related cardiotoxicity was observed.

The dosages involved in this Example were calculated based on the free base of Compound I.

Example 6 Therapeutic Effects of the Capsules of Dihydrochloride of Compound I on Leiomyosaroma of Soft Tissue (1) Patient's Medical History Male, born in 1963, leiomyosaroma of soft tissue, the pathological stage was T2bN0M1, and the clinical stage was stage IV.

Surgical treatment was carried out in November 2008, the treatment of ADM (adriamycin)+IFO (ifosfamide) was performed from November 2008 to May 2009; the chemotherapy was failed in May 2009; the chemotherapy was continued from January 2012 to Mar. 1, 2013, and CT indicated the progress of tumours. The abdominal radiotherapy was carried out from November 2012 to January 2013, without the therapeutic effect evaluation.

From May 21, 2013, the capsules of dihydrochloride of Compound I were taken at 12 mg once daily, and the administration was continuously performed for 2 weeks and rested for 1 week, i.e., 3 weeks (21 days) was a treatment cycle.

(2) Tumour Baseline Evaluation Results

| Time | Sum of the longest diameter of target lesions (right retroperitoneal masses) (mm) |
|---|---|
| Before treatment | 34 |
| Treatment with the capsules of dihydrochloride of Compound I for 2 cycles | 32 |
| Treatment with the capsules of dihydrochloride of Compound I for 8 cycles | 25 |
| Treatment with the capsules of dihydrochloride of Compound I for 20 cycles | 20 |

After the patient was administrated for 8 cycles, the longest diameter of target lesions decreased 26.47%, and the evaluation result was SD (stable); and, after the patient was administrated for 20 cycles, the longest diameter of target lesions decreased 41.18%, and the evaluation result was PR (partial remission), and non-target lesions had no progression. During administration, the adverse reactions were basically tolerable, and the main adverse events were elevation of blood pressure, abnormal triglyceride, proteinuria, hand-foot skin reaction and the like, and no drug-related cardiotoxicity was observed.

The dosages involved in this Example were calculated based on the free base of Compound I.

Example 7 Therapeutic Effects of the Capsules of Dihydrochloride of Compound I on Alveolar Soft-Part Sarcoma (1) Patient's Medical History Male, born in 1993; pathological diagnosis: alveolar soft-part sarcoma with necrosis, striated muscle tissue was invaded by the tumour, pG2T2bM1;

clinical diagnosis: alveolar soft-part sarcoma in the left gluteus maximus, hepatic metastasis, lung metastasis and bone metastasis after surgery, stage IV.

The patient was performed resection of the mass in the left hip in August 2012; from Aug. 22, 2012 to Sep. 20, 2012, the chemotherapy regimen of IFO (ifosfamide)+ADM (adriamycin) was administrated, without gastrointestinal reaction; on Oct. 26, 2012, the chemotherapy regimen of IFO (ifosfamide)+EPI (epirubicin) was administrated, without gastrointestinal reaction and bone marrow suppression. On Nov. 26, 2012, the therapeutic effect evaluation was stable (SD); and on Nov. 29, 2012, the chemotherapy regimen of IFO (ifosfamide)+EPI (epirubicin) was administrated.

From Jan. 4, 2013 to Mar. 20, 2013, the chemotherapy regimen of PTX (paclitaxel)+DDP (cisplatin) was administrated. On Jul. 29, 2013, intrahepatic metastasis was evaluated as stable, the condition of double-pulmonary metastasis was evaluated as progression (PD), and the chemotherapy regimen of PTX (paclitaxel)+DDP (cisplatin) was continued. On Sep. 13, 2013, the condition was evaluated as stable, the chemotherapy regimen of PTX (paclitaxel)+DDP (cisplatin) was performed, without bone marrow suppression as well as liver and kidney function damage.

From Jan. 1, 2014, the capsules of dihydrochloride of Compound I were taken at 12 mg once daily, and the administration was continuously performed for 2 weeks and rested for 1 week, i.e., 3 weeks (21 days) was a treatment cycle.

(2) Tumour Baseline Evaluation Results

| Time | Sum of the longest diameter of target lesions (mm) | Posterior basal segment of lower lobe in the left lung (mm) | Medial basal segment of lower lobe in the left lung (mm) |
|---|---|---|---|
| Before treatment | 58 | 36 | 22 |
| Treatment with the capsules of dihydrochloride of Compound I for 2 cycles | 45 | 29 | 16 |
| Treatment with the capsules of dihydrochloride of Compound I for 4 cycles | 37 | 24 | 13 |
| Treatment with the capsules of dihydrochloride of Compound I for 8 cycles | 29 | 18 | 11 |

After the patient was treated for 2 cycles, the sum of the longest diameter of target lesions decreased 22.41%; after the patient was treated for 4 cycles, the sum of the longest diameter of target lesions decreased 36.21%, PR (partial remission) was achieved, and thus the therapeutic effects were significant; and after the patient was treated for 8 cycles, the sum of the longest diameter of target lesions decreased 50%, PR (partial remission) was achieved, and thus the therapeutic effects were significant. When the patient was cumulatively treated for 513 days, non-target lesions had no progression, the patient was not out of the group and had obvious tumor response, and clinical manifestations could be tolerated. During treatment, the test adverse reactions were basically tolerable, and the main adverse events were increased TSH (thyroid stimulating hormone), hand-foot skin reaction, abnormal triglyceride and the like, and no drug-related cardiotoxicity was observed.

The dosages involved in this Example were calculated based on the free base of Compound I.

Example 8 Therapeutic Effects of the Capsule of Dihydrochloride of Compound I on Epithelioid Sarcoma (1) Patient's Medical History Male, born in 1960, pathological diagnosis: epithelioid sarcoma; TNM stage: G2TxM1; clinical diagnosis: proximal-type epithelioid sarcoma in perineum; clinical stage: stage III Surgery:

In June 2003, excision of masses in perineum was carried out; in December 2011, a puncture of the paravertebral masses was carried out; and in June 2013, extended resection of masses in perineum was carried out.

The History of Chemotherapy:

In October 2005, the VAD chemotherapy regimen (vincristine+adriamycin+dexamethasone) and the MVAD chemotherapy regimen (melphalan+vincristine+adriamycin+dexamethasone) were performed 6 times, supplemented with radiotherapy. Afterwards, the patient received chemotherapy in hospital, mainly the VAD regimen (vincristine+adriamycin+dexamethasone), once per 3-6 months, and the last time was November 2011. On Nov. 16, 2011, the DCEP chemotherapy regimen (cyclophosphamide+dexamethasone+etoposide+cisplatin) was administrated. From February 2012 to March 2012, the chemotherapy regimen of ADM (adriamycin)+IFO (ifosfamide) was administrated three times. In April 2012, the chemotherapy regimen of ADM (adriamycin)+IFO (ifosfamide) was administrated, Grade I bone marrow suppression occurred, and no obvious liver and kidney function damage was observed. On Aug. 9, 2013, the chemotherapy regimen of PTX (paclitaxel)+Gemzar (gemcitabine hydrochloride) was administrated. On Aug. 17, 2013, the chemotherapy regimen of Gemzar (gemcitabine hydrochloride) was administrated. On Aug. 31, 2013, the chemotherapy regimen of PTX (paclitaxel)+Gemzar (gemcitabine hydrochloride) was administrated. On Sep. 10, 2013, the chemotherapy regimen of Gemzar (gemcitabine hydrochloride) was administrated. On Sep. 25, 2013, the chemotherapy regimen of PTX (paclitaxel)+Gemzar (gemcitabine hydrochloride) was administrated. On Oct. 5, 2013, the chemotherapy regimen of Gemzar (gemcitabine hydrochloride) was administrated. On Oct. 18, 2013, the chemotherapy regimen of PTX (paclitaxel)+Gemzar (gemcitabine hydrochloride) was administrated. The best therapeutic effect was progression of disease (PD).

The History of Radiotherapy:

From Dec. 20, 2011 to Jan. 18, 2012, palliative radiotherapy was performed against thoracic vertebral metastasis (T6-12), and DT was administrated up to 39.6 Gy/22 times/4.5 w.

Other Antitumor Therapy:

On Mar. 12, 2013 and Mar. 30, 2013, the hypoecho masses in perineum were treated with HIFU (high-intensity focused ultrasound) twice.

From Mar. 12, 2014, the capsules of dihydrochloride of Compound I were taken at 12 mg once daily, and the administration was continuously performed for 2 weeks and rested for 1 week, i.e., 3 weeks (21 days) was a treatment cycle.

(2) Tumour Baseline Evaluation Results

| Time | Sum of the longest diameter of target lesions (mm) | Lymph nodes of the right groin (mm) | Lymph nodes of the right iliac vessel (mm) |
|---|---|---|---|
| Before treatment | 73 | 19 | 54 |
| Treatment with the capsules of dihydrochloride of Compound I for 2 cycles | 77 | 23 | 54 |
| Treatment with the capsules of dihydrochloride of Compound I for 6 cycles | 84 | 26 | 58 |

After the patient was treated for 6 cycles, the sum of the longest diameter of target lesions increased 15.07%, the therapeutic effect was evaluated as SD (stable disease), and the tumour had been continuously controlled. The patient had been cumulatively treated for 420 days, non-target lesions had no progression, the patient had no new lesion and was not out of the group, the tumours were under a continuous control, and clinical manifestations could be tolerated. During the treatment, the test adverse reactions were basically tolerable, and the main adverse events were increased TSH (thyroid stimulating hormone), elevation of blood pressure, abnormal triglyceride and the like, and no drug-related cardiotoxicity was observed. The dosages involved in this Example were calculated based on the free base of Compound I.

What is claimed is:

1. A method for treating a soft tissue sarcoma, the method comprising administrating Compound I or a pharmaceutically acceptable salt thereof to a patient in need of treatment, wherein the soft tissue sarcoma is selected from malignant fibrous histiocytoma, fibrosarcoma, liposarcoma, leiomyosarcoma, rhabdomyosarcoma, synovial sarcoma, dermatofibrosarcoma protuberans, malignant peripheral nerve sheath tumor, alveolar soft part sarcoma, clear cell sarcoma, hemangiosarcoma, malignant mesenchymoma, epithelioid sarcoma and undifferentiated sarcoma,

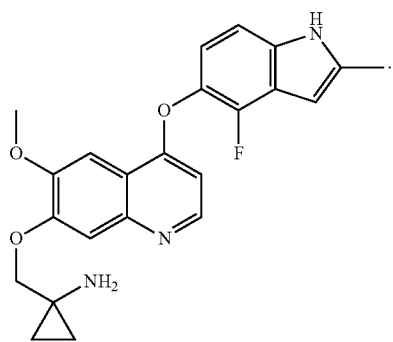

Compound I

2. The method according to claim 1, wherein the soft tissue sarcoma is an advanced soft tissue sarcoma.

3. The method according to claim 1, wherein the pharmaceutically acceptable salt comprises a hydrochloride of Compound I.

4. The method according to claim 1, wherein the daily dosage of the Compound I or the pharmaceutically acceptable salt thereof is 2 mg-20 mg.

5. The method according to claim 1, wherein Compound I or the pharmaceutically acceptable salt thereof is administrated by an interval administration, and the interval administration includes administration periods and rest periods, wherein the ratio of the administration periods to the rest periods in days is 2:0.5-5.

6. The method according to claim 1, wherein the soft tissue sarcoma is selected from leiomyosarcoma, synovial sarcoma and alveolar soft part sarcoma.

7. The method according to claim 6, wherein the soft tissue sarcoma is an advanced soft tissue sarcoma.

8. The method according to claim 6, wherein the soft tissue sarcoma is an advanced soft tissue sarcoma which has been treated with chemotherapy.

9. The method according to claim 6, wherein the pharmaceutically acceptable salt comprises a hydrochloride of Compound I.

10. The method according to claim 6, wherein the pharmaceutically acceptable salt comprises a dihydrochloride of Compound I.

11. The method according to claim 6, wherein the daily dosage of the Compound I or the pharmaceutically acceptable salt thereof is 2 mg-20 mg.

12. The method according to claim 6, wherein Compound I or the pharmaceutically acceptable salt thereof is administrated by an interval administration, and the interval administration includes administration periods and rest periods, wherein the ratio of the administration periods to the rest periods in days is 2:0.5-5.

13. The method according to claim 1, wherein the soft tissue sarcoma is an advanced soft tissue sarcoma which has been treated with chemotherapy.

14. A method of treating a soft tissue sarcoma, the method comprising administering to a patient in need thereof a pharmaceutical composition comprising a therapeutically effective amount of Compound I or a pharmaceutically acceptable salt thereof, and at least one pharmaceutically acceptable carrier, wherein the soft tissue sarcoma is selected from leiomyosarcoma, synovial sarcoma and alveolar soft part sarcoma,

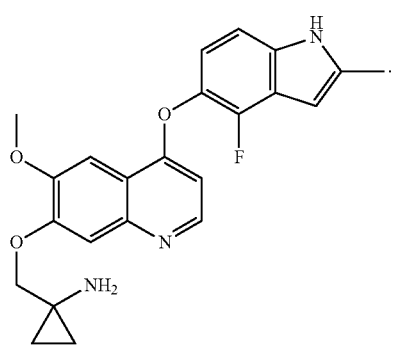

Compound I

15. The method according to claim 14, wherein the soft tissue sarcoma is an advanced soft tissue sarcoma that has been treated with chemotherapy.

16. The method according to claim 14, wherein the pharmaceutically acceptable salt comprises a hydrochloride of Compound I.

17. The method according to claim 14, wherein the pharmaceutical composition is a single dosage comprising 2 mg to 20 mg of Compound I or a pharmaceutically acceptable salt thereof.

18. The method according to claim 14, wherein the composition is administrated by an interval administration, and the interval administration includes administration periods and rest periods, wherein the ratio of the administration periods to the rest periods in days is 2:0.5-5.

19. The method according to claim 1, wherein the soft tissue sarcoma is selected from malignant fibrous histiocytoma, fibrosarcoma, liposarcoma, leiomyosarcoma, synovial sarcoma, alveolar soft part sarcoma, clear cell sarcoma, and epithelioid sarcoma.

20. The method according to claim 14, wherein the composition is administrated continuously for 2 weeks and withdrawn for 1 week.

\* \* \* \* \*